United States Patent [19]

Christiansen et al.

[11] Patent Number: 4,621,522

[45] Date of Patent: Nov. 11, 1986

[54] METHOD OF DETERMINING THE MINIMUM LEVEL OF GAS ENRICHMENT FOR A MISCIBLE FLOOD

[75] Inventors: Richard L. Christiansen; Hiemi Kim, both of Littleton, Colo.

[73] Assignee: Marathon Oil Company, Findlay, Ohio

[21] Appl. No.: 776,725

[22] Filed: Sep. 16, 1985

Related U.S. Application Data

[63] Continuation-in-part of Ser. No. 770,819, Aug. 28, 1985.

[51] Int. Cl.$^4$ .............................................. G01N 15/00
[52] U.S. Cl. .................................................. 73/61 R
[58] Field of Search .................... 73/64.4, 61 R, 64.2, 73/61.1 R, 19, 53

[56] References Cited

U.S. PATENT DOCUMENTS

| | | | |
|---|---|---|---|
| 3,276,844 | 10/1966 | Davison et al. | 23/253 |
| 3,300,385 | 1/1967 | Danon | 167/84.5 |
| 4,455,860 | 6/1984 | Cullick et al. | 73/19 |

OTHER PUBLICATIONS

W. F. Yelling and R. S. Metcalfe, Determination and Prediction of $CO_2$ Minimum Miscibility Pressures, *J. Pet. Technology*, pp. 160–168, Jan. 1980.

Technical Disclosure Bulletin, vol. XXI, Marathon Oil Company, Findlay, Ohio, p. 13, 1981.

G. C. Wang and E. V. Knight, Visual Study of Miscibility Development of $CO_2$-Crude Systems, 2nd Ass. Rech. Tech. Exploit Petrol. Enhanced Oil Recovery Europe Symp., (Paris, 82.11.08–10), Proc., pp. 269–278, 1982.

G. C. Wang, Determination of Miscibility Pressure by Direct-Observation Method, DOE/MC/16140-T2, pp. 1–13, 1982.

*Primary Examiner*—Stephen A. Kreitman
*Assistant Examiner*—Hezron E. Williams
*Attorney, Agent, or Firm*—Rodney F. Brown; Jack L. Hummel

[57] ABSTRACT

A method of determining the minimum level of enrichment required to render a substantially immiscible gas miscible in a liquid hydrocarbon by observing the behavior of enriched gas bubbles having incrementally increasing levels of enrichment as they rise through samples of liquid hydrocarbon. The lowest level of enrichment at which a bubble is observed to dissipate in the liquid hydrocarbon is the minimum level of enrichment.

35 Claims, 4 Drawing Figures

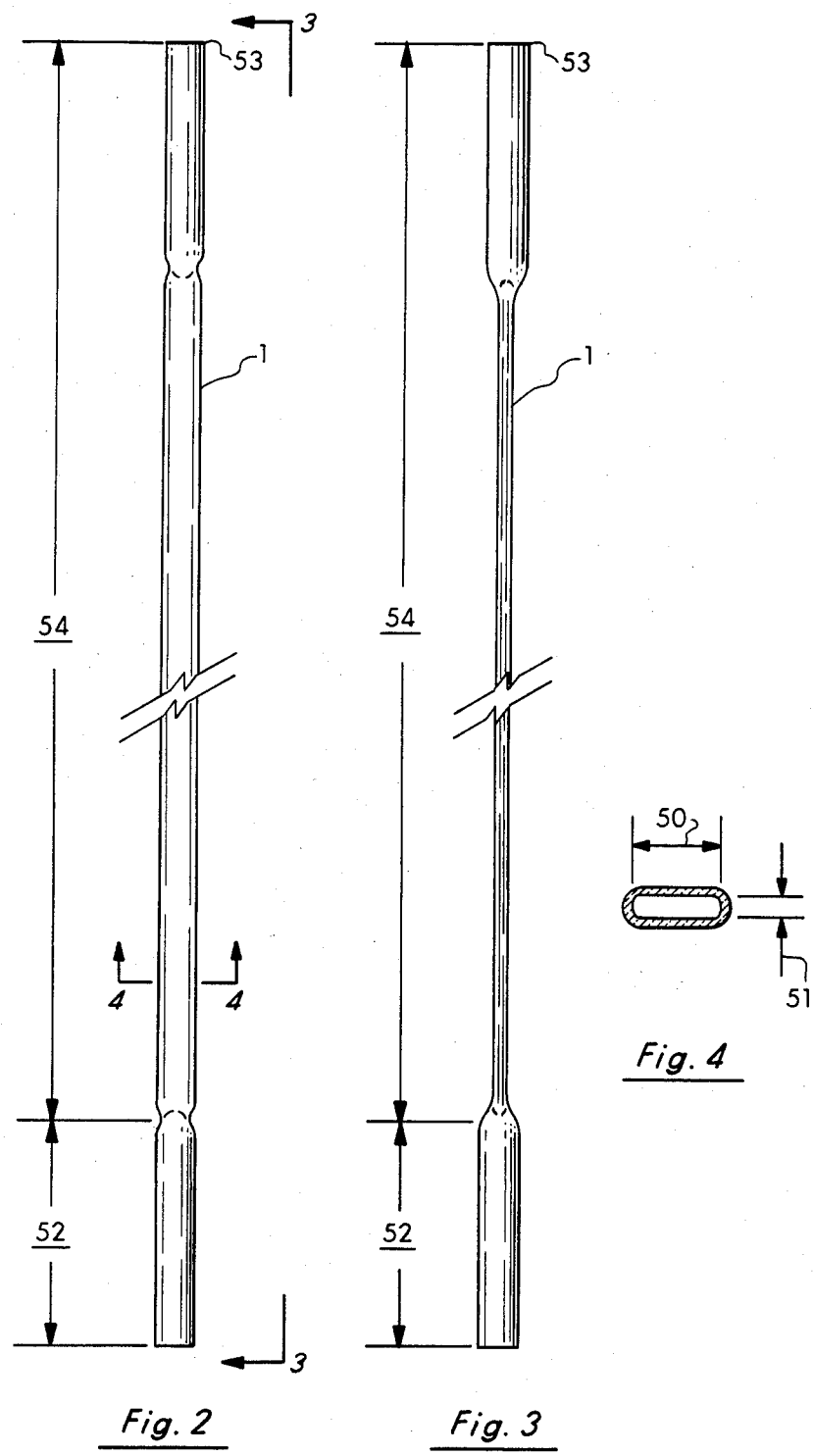

METHOD OF DETERMINING THE MINIMUM LEVEL OF GAS ENRICHMENT FOR A MISCIBLE FLOOD

This application is a continuation-in-part application of parent application Ser. No. 770,819 filed on Aug. 28, 1985, and titled, "Apparatus and Method for Determining the Minimum Miscibility of a Gas in a Liquid."

BACKGROUND OF THE INVENTION

1. Technical Field

The invention relates to a method for predetermining the composition of a gas flood used in an enhanced oil recovery process and, more particularly, for determining the minimum level of enrichment required to render a substantially immiscible gas miscible in a crude oil.

2. Description of Related Art

In a gas flood employing a condensing gas drive, intermediate hydrocarbon components in the injected gas condense upon contact with the crude oil in place at the formation temperature and pressure. The condensed hydrocarbon intermediates mix with the crude oil in situ, thereby altering the crude oil composition. If sufficient hydrocarbon intermediates condense from the gas and mix with the oil, the flooding gas and the oil in place ultimately become miscible. This effect is termed a miscible condensing gas drive and it substantially enhances oil recovery from the formation.

Many gases presently employed as flooding gases do not contain sufficient hydrocarbon intermediates to achieve miscibility with the crude oil at formation conditions, i.e., the flooding gases are substantially immiscible in the crude oil. In order to achieve miscibility in the crude oil, it is necessary prior to injection to artificially enrich the flooding gas, termed bulk gas hereafter, with hydrocarbon intermediates contained in an enriching fluid.

The resulting enriched gas is a multicomponent gas comprised of the bulk gas and the enriching fluid. The enriched gas has sufficient hydrocarbon intermediates to render it substantially miscible in the oil upon extended multiple contacting. Since the enriching fluid is often considerably more expensive than the bulk gas, it is desirable to achieve the miscible condensing gas drive using a minimum quantity of the enriching fluid. Thus, determination of the minimum level of enrichment required to render a substantially immiscible gas miscible in a crude oil in place is critical to the operation of a miscible gas flood.

The slim tube method is a widely accepted method for determining the minimum level of enrichment required to render a gas miscible in a crude oil. A slim tube is a long narrow tube approximately 12.2 to 18.3 meters long and having an inside diameter of 0.64 cm or less and packed with an unconsolidated material such as sand or glass beads. The tube is saturated with oil and thereafter flooded with a gas having a given level of enrichment and at constant pressure and temperature. The oil recovery is determined at that level of enrichment and then similar floods are conducted at different levels of enrichment. The oil recovery at each level of enrichment is measured as a function of the volume of gas injected. The oil recovery efficiency is determined thereafter as a function of the enrichment level. The minimum level of enrichment, as determined by the slim tube method, is the level of enrichment above which there is very little increase in oil recovery efficiency.

The slim tube method is extremely time-consuming, taking several days to determine the minimum level of enrichment required for a single gas-crude oil system.

As such, an accurate and more rapid method is needed for determining the minimum level of enrichment required for a gas used in a miscible condensing gas drive.

SUMMARY OF THE INVENTION

The present invention relates to a method of determining the minimum level of enrichment required to render a substantially immiscible bulk gas miscible in a liquid hydrocarbon. The apparatus employed in the method of the present invention is a rising bubble apparatus (RBA) comprised of a transparent vessel termed a sight gauge, a bubble injection means, and a pressure maintenance means. The sight gauge has a transparent tube mounted therein which contains a liquid hydrocarbon of interest and enables visual observation of gas bubbles passing through the liquid.

According to the method of the invention the tube is filled with a liquid hydrocarbon sample, such as crude oil. The tube is maintained at a substantially fixed pressure by a hydraulic fluid in the vessel. An enriched gas sample, having a level of enrichment below the minimum level and comprised of the bulk gas and an enriching gas, is injected into the vessel. A bubble of enriched gas is formed at the bottom of the tube and the buoyant force on the bubble cause it to rise up through the oil. The behavior of the individual bubble is observed as it rises. This sequence is repeated for a series of several bubbles, constituting an experimental run.

Thereafter, a second experimental run is conducted. The used oil sample is flushed from the tube and replaced with a fresh oil sample having the same composition as the first. A series of bubbles from a fresh enriched gas sample, having an incrementally higher level of enrichment than the enriched gas of the previous run, is launched through the fresh oil sample in the same manner as above and at the same pressure.

The experimental runs are repeated as often as necessary, each time incrementally increasing the level of enrichment of the bulk gas, until at least one bubble in a series is first observed to substantially dissipate in the oil. This point is termed the minimum level of enrichment required to render the bulk gas miscible in the liquid hydrocarbon. At the minimum level, the interfacial tension between the bubble and the liquid hydrocarbon approaches zero.

The present method quickly and accurately enables one to determine the minimum level of enrichment required to render substantially any immiscible gas miscible in substantially any liquid hydrocarbon simulating the multiple contact miscibility mechanism believed to occur in an oil-bearing subterranean formation. Determination of an accurate minimum level of enrichment enables one to optimize the cost and oil recovery efficiency of a miscible gas flood using a condensing gas drive.

BRIEF DESCRIPTION OF THE DRAWINGS

FIG. 2 is a frontal view of one embodiment of the glass tube.

FIG. 3 is a side view of the glass tube of FIG. 2.

FIG. 4 is a cross-sectional view of the glass tube of FIG. 2.

DESCRIPTION OF THE PREFERRED EMBODIMENTS

Figure 1:
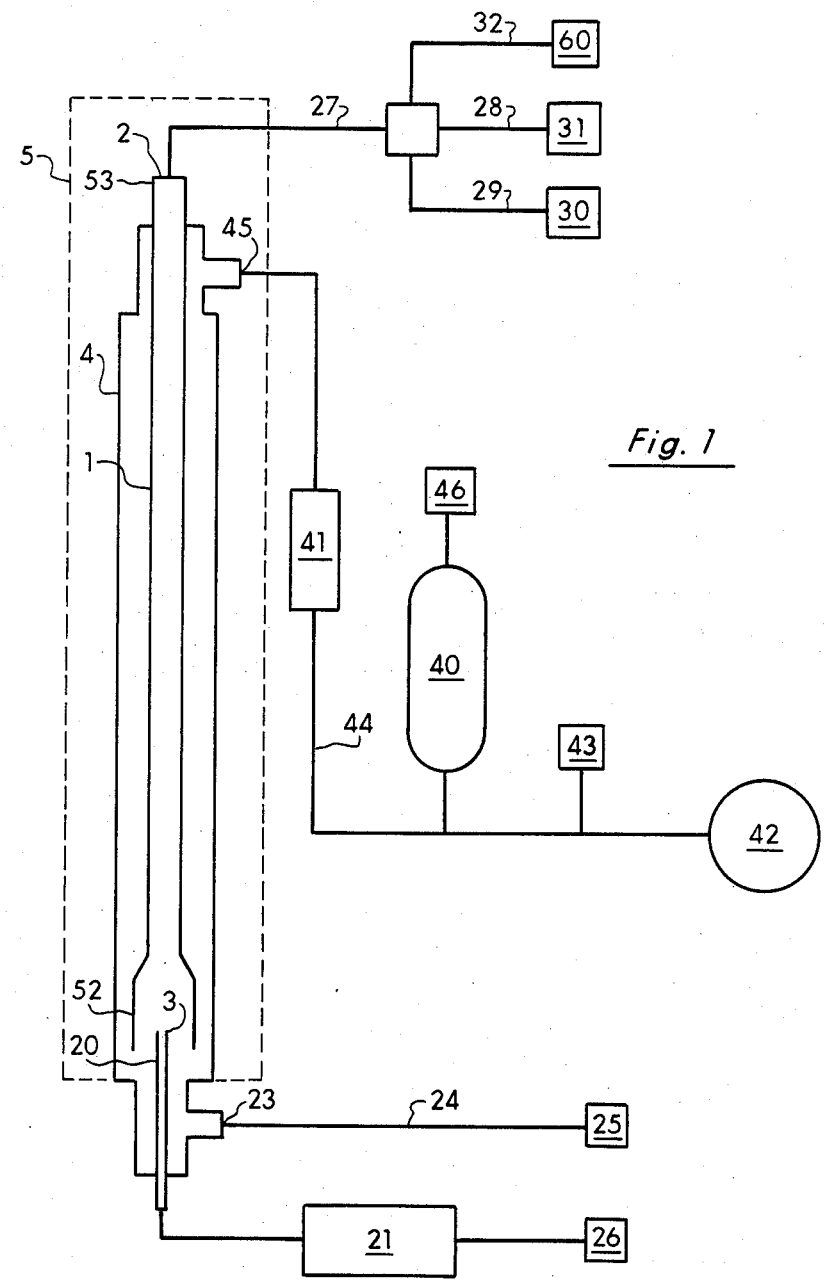
FIG. 1 is a schematic drawing of the rising bubble apparatus used in the method of the present invention.

The minimum level of enrichment is defined as the level of gas enrichment at which the interfacial tension at an interface between an enriched gas bubble and a continuous liquid hydrocarbon approaches zero, causing the bubble to substantially dissipate in the liquid. In practice, the interfacial tension at the interface between the bubble and the liquid is not exactly zero at the minimum level of enrichment because a number of fluid mechanic effects may cause the bubble to dissipate before an interfacial tension of exactly zero is reached. However, for practical purposes the sum of the effects is very small relative to the interfacial tension. Thus, an interfacial tension of zero at the minimum level of enrichment is a good approximation.

The liquid hydrocarbon described herein is preferably a crude oil obtained from a subterranean oil-bearing formation of interest. The enriched gas is comprised of a bulk gas and an enriching fluid. The bulk gas is substantially any gas which has a minimum miscibility pressure in the liquid hydrocarbon above the formation fracturing pressure or the anticipated operating pressure of a flood and at the formation temperature. Examples of the bulk gas include $CO_2$, $N_2$, $SO_2$ and lean natural gas, i.e., methane.

The enriching fluid is an intermediate hydrocarbon, i.e., a hydrocarbon having a molecular weight greater than methane and preferably less than decane. Such fluids include ethane, propane, butane, etc., and mixtures thereof. The enriching fluids are often liquids as pure components. However, when the enriching fluid is a component of the enriched gas, it remains in the gas phase until it contacts the liquid hydrocarbon. The enriching fluid is substantially miscible in the bulk gas and is preferably more miscible than the bulk gas in the liquid hydrocarbon due to a lower miscibility pressure.

The rising bubble apparatus (RBA) shown in FIG. 1 and used in the method of the present invention is comprised of a transparent tube 1 mounted in a transparent high pressure vessel 4 termed a sight gauge. Tube 1 has a longitudinal axis perpendicular to its cross-section. Tube 1 is mounted such that the longitudinal axis deviates from the horizontal at an angle greater than 0° up to about 90°. The geometry of the tube cross-section is not critical, but the cross-sectional area of the tube must be sufficiently large to enable a visible bubble to pass through it. At the same time the depth of the cross-section is limited by the opacity of the liquid therein. For example, the maximum cross-sectional depth at which a bubble is visible in a dark crude oil is about 1 mm. Thus, a tube having an elongated cross-section substantially wider than it is deep is preferred for viewing relatively opaque liquids such as dark crude oils. This configuration maximizes the cross-sectional area while minimizing the depth of the tube. Examples of such cross-sections include rectangles, ovals, ellipes, and the like.

An embodiment of tube 1 is shown in FIGS. 2, 3, and 4. FIGS. 2 and 3 are actual size. FIG. 4 is enlarged to a scale of 3:1. Tube 1 has an upper section 54 which is the bubble-liquid contacting portion of the tube and a lower section 52 which is the bubble-forming portion of the tube. Upper section 54 is substantially longer than lower section 52. Tube 1 is substantially rectangular in cross-section throughout except for cylindrical lower section 52 and a cylindrical portion near the top end 53 of tube 1. The cross section has an inside width 50 of 0.5 cm and depth 51 of 0.1 cm. The aspect ratio of the tube which is the width divided by depth is 5, lower section 52 of tube 1 is about 3.8 cm long and cylindrical, having an inside diameter of about 0.5 cm. Lower section 52 is flared and open to the interior of vessel 4 to enable bubble formation therein. A fitting 2 is placed over top end 53 of tube 1 to accommodate a line 27 and prevent direct fluid communication between tube 1 and vessel 4 via top 53. The portion of tube 1 near top 53 is flared in the same manner as lower section 52 solely to accommodate fitting 2.

A hollow 16-gauge needle 20 is directed into the opening of lower section 52. Needle 20 has a tip 3 which preferably penetrates into the interior of lower section 52. Alternatively tip 3 is located in vessel 4 directly below the opening. Needle 20 communicates with an external gas source 26 by a metering means 21, such as a syringe or metering pump. Metering means 21 regulates the flow of gas through needle 20 into lower section 52 and enables the formation of bubbles having constant volume. Bubble sizes may be varied using needles 20 of differing diameters.

Top end 53 of tube 1 is not open to vessel 4, but tube 1 communicates with a liquid sample source 30, containing fresh liquid samples, via a liquid sample line 29. Tube 1 also communicates with a solvent source 31, containing cleaning solvents such as heptane or toluene by means of a solvent line 28. Sample and solvent lines 28 and 29 are merged into a single line 27 which enters top end 53 of tube 1. Line 32 also merges with line 27 as an offtake to expel used liquid samples from tube 1 and gas bubbles from line 27. Line 32 is fitted with a back pressure regulator 60 to facilitate the expulsion of gas bubbles.

A pressure maintenance means 40 provides a pressure regulating supplement to back pressure regulator 60. Pressure maintenance means 40 is in fluid communication with vessel 4 via a line 44 into a pressure maintenance port 45 in vessel 4. In the preferred embodiment the pressure maintenance means 40 is a reservoir containing a hydraulic fluid which maintains a preselected pressure on the liquid sample in tube 1 at the outset of the experimental runs. Reservoir 40 allows small volumes of liquid or gas to be injected into the fixed volume of vessel 4 with only small increases in pressure by maintaining a pressurized gas head 46 over the hydraulic fluid in reservoir 40. A surge valve 41 may be installed in the hydraulic fluid line 44 between reservoir 40 and vessel 4 to shut off line 44 should vessel 4 rupture. Line 44 is also connected to a pressure gauge 42 and a hydraulic fluid source 43 should it become necessary to add fluid to reservoir 40 or vessel 4. A second hydraulic fluid port 23 may be provided in vessel 4 for adding additional fluid from source 25 to vessel 4 or withdrawing fluid via line 24.

Vessel 4 is in temperature bath 5 such as a heated mineral oil to enable strict temperature control of the process. Bubble injection means 20 may also have a heating means to prevent condensation of the pressurized gas therein.

The actual materials used for vessel 4 and tube 1 may vary. However, it is critical that vessel 4 and tube 1 be transparent to allow visual observation and that vessel 4 be able to withstand the operating pressure differential across its walls. Glass is the material of choice, although transparent plastics may also be used. Further, it is preferred that all remaining wetted parts of the RBA be of stainless steel or glass.

The RBA is operated by filling the transparent vessel 4 and the tube 1 with the hydraulic fluid via line 44 and/or 24. The hydraulic fluid may be the same fluid as the liquid sample, but is preferably substantially any other fluid which is inert in the gases and liquids being tested, relatively immiscible in the liquid sample at the experimental conditions, and results in an interfacial tension between it and the gas which is greater than that between the liquid sample and the gas to promote formation of sufficiently large visible bubbles. Exemplary hydraulic fluids include water, methanol and mercury.

The liquid sample, i.e., crude oil in this case, is added to tube 1 via line 27 and displaces the hydraulic fluid, water, from tube 1. However, an amount of water is preferably retained in flared lower section 52 of tube 1 sufficient to immerse tip 3 of needle 20. The interface between the water and the liquid sample is maintained substantially constant by expelling spent bubbles via regulator 60 as they accumulate in line 27. The pressure in vessel 4 and tube 1 is adjusted to a predetermined level below the MMP by adding or removing water via line 44 and/or 24. The pressure is maintained by back pressure regulator 60 as well as gas head 46 in pressure reservoir 40. The gas is a compressible gas, such as nitrogen, which is not soluble in the hydraulic fluid to a significant degree.

An enriched gas sample having a level of enrichment below the minimum level is prepared. The enriched gas may be prepared by metering the enriching fluid and bulk gas from separate sources into a common line and mixing them in-line. Alternatively, a number of enriched gas samples having different levels of enrichment can be premixed in individual sample tanks. A separate sample tank containing premixed enriched gas as shown in FIG. 1 is used for each run as the external gas source 26.

The enriched gas is metered into needle 20 to form a series of bubbles of fixed volume in the water at tip 3. A preferred bubble volume enabling visibility in tube 1 of FIG. 2 is about 0.03 cubic centimeters. Each bubble rises from tip 3 under its buoyant force, through the water in lower section 52, across the water-oil interface, and up through the oil column of upper section 54.

Where a tube having an elongated cross-section is used, such as in FIG. 2, the bubbles maintain substantial contact with the interior wall of upper section 54, enhancing their visibility. In some cases it may be desirable to pretreat the tube walls with a chemical agent to render them oil or water wet before adding any liquids. The glass tube is preferably coated with an agent, such as DRI-FILM, a trademark of The General Electric Co., Fairfield, CT, USA, which is a transparent silicon resin solution. The agent renders the glass surface oil wet and prevents bubbles formed in the water from adhering to the glass surface of tube 1.

The shape and motion of each bubble are observed as the bubble passes through the oil. In the preferred method, only one bubble is present in tube 1 at a time. This is accomplished by metering the enriched gas into needle 20 at predetermined time intervals. Thus, each bubble can be observed individually. The bubbles may be photographed with a still, video or motion picture camera. Backlighting of tube 1 enhances visual observation and photography.

As noted above, the spent gas bubble accumulating in closed line 27 after exiting upper section 54 can be released via back pressure regulator 60. After a series of bubbles have risen through the column of oil concluding an experimental run, the used oil sample is flushed from tube 1 out lines 27 and 32 using water injected via lines 23 or 44. Tube 1 is rinsed with a solvent from source 31 via lines 28 and 27 to clean any remaining oil from the tube walls. The solvent is then flushed out through lines 27 and 32 with water and replaced by a fresh oil sample from source 30 via lines 29 and 27.

The procedure is repeated as often as necessary, each time incrementally increasing the level of enrichment, until at least one enriched gas bubble is observed to substantially dissipate in the oil before it reaches the top of the tube. By substantially dissipate, it is meant that the bubble spontaneously condenses in the oil and is not substantially visible. The level of gas enrichment in the run where dissipation occurs is observed to be the minimum level of enrichment required to render the substantially immiscible bulk gas miscible in the liquid hydrocarbon. The value for the minimum level of enrichment so determined is utilized by the skilled practitioner to design a miscible condensing gas drive.

The mechanism by which it is believed the enriched gas becomes miscible in the liquid hydrocarbon is termed multiple contact miscibility. According to this mechanism, the gas initially contacting the oil is fresh enriched gas containing intermediate hydrocarbon components. Although the gas and liquid are not immediately miscible upon first contact, the intermediate hydrocarbon components in the gas bubble condense on first contact with the oil at the bottom of the tube. The condensed components migrate by mass transfer across the interface between the oil and the gas bubble into the oil. The condensed hydrocarbon components migrating into the oil change the composition of the oil. As additional gas bubbles are injected into the tube, the oil continuously contacts fresh gas and continuously accepts intermediate hydrocarbon components from the bubbles.

Below the minimum level of enrichment, the gas bubbles stripped of intermediate hydrocarbon components may shrink significantly, but will still retain a visible volume, as they pass through the tube. However, at the minimum level of enrichment, a sufficient quantity of hydrocarbon components enter the oil from the gas bubbles to finally render the oil miscible in the gas. Once multiple contact miscibility is achieved, subsequent enriched gas bubbles will substantially dissipate in the oil almost immediately. As used herein, where fluids are termed "miscible" or "immiscible" in the liquid hydrocarbon, they are referred to as such in the context of a multiple contact miscibility mechanism.

The actual quantity of intermediate hydrocarbon components entering the oil from the bubble by mass transfer is a strong function of the temperature and pressure of the system and to a lesser extent the contact time. The pressure is preferably maintained constant within a pressure range below the fracturing pressure of the formation to be flooded and the temperature is preferably maintained constant at the temperature of the formation to be flooded. The tube holding the oil in the present method is long enough in most cases by design to provide a sufficient contact time, even when mounted at a 90° angle from the horizontal, to dissipate the bubble in the oil and the minimum level of enrichment. However, should a longer contact time be required, the tube can be slanted to a smaller angle from the horizontal. As the deviation angle becomes closer to the horizontal, the buoyant force is reduced and the contact time is increased.

The parameters of the tube geometry and bubble size are generally considerations only with respect to their effect on the visibility of the bubble in the liquid. In all cases the design and operating parameters must be selected such that the gas bubble is readily visible in the oil.

The following examples are illustrative of the method of the present invention but are not to be construed as limiting the scope thereof.

EXAMPLE 1

The minimum level of enrichment required to render an enriched gas comprised of a methane bulk gas and an n-butane enriching fluid in liquid decane is determined according to the following method. Methane, which is substantially immiscible in decane at the desired conditions, is enriched with n-butane to a level below the minimum level of enrichment. Decane is charged to the tube of the RBA and maintained at a temperature of 71° C. and a pressure of 20700 kPa. 10 bubbles of the enriched gas are discharged into the decane at spaced intervals. The behavior of the bubbles are observed as they pass through the tube to the top. The stripped enriched gas bubbles and oil are then discharged from the tube and the experiment is repeated with a fresh oil sample and enriched gas bubbles having an incrementally higher level of enrichment than the first series of bubbles. The results of these and succeeding runs are shown in Table 1 below.

TABLE 1

| Enriched Gas Composition (mole fraction) | | |
|---|---|---|
| Methane | n-Butane | Observations |
| 0.92 | 0.08 | Bubbles slowly shrink while rising in the tube. |
| 0.88 | 0.12 | Bubbles slowly shrink while rising in the tube. |
| 0.84 | 0.16 | First four bubbles shrink while rising in the tube. The fifth and subsequent bubbles rapidly condense upon contact with the oil. |
| 0.80 | 0.20 | First three bubbles shrink while rising in the tube. The fourth and subsequent bubbles rapidly condense upon contact with the oil. |

The minimum level of enrichment required to render methane miscible in decane by a multiple contact miscibility mechanism at the stated temperature and pressure conditions is experimentally determined to be a 0.16 mole fraction n-butane in methane. This is the lowest level of enrichment at which the enriched methane bubble is observed to dissipate in the decane.

EXAMPLE 2

The minimum level of enrichment required to render an enriched gas comprised of a methane bulk gas an an ethane enriching gas in a crude oil at 116° C. and 34500 kPa is determined according to the method of Example 1. The crude oil has an API specific gravity of 35, bubblepoint pressure of 13400 kPa and a gas-oil ratio of 400 standard cubic feet per stock tank barrel. The results are shown below in Table 2.

TABLE 2

| Enriched Gas Composition (mole fraction) | | |
|---|---|---|
| Methane | Ethane | Observations |
| 0.91 | 0.09 | Bubbles slowly shrink while rising in tne tube. |
| 0.88 | 0.12 | First six bubbles slowly shrink while rising in the tube. The seventh and subsequent bubbles condense upon contact with the oil. |
| 0.83 | 0.17 | First five bubbles slowly shrink while rising in the tube. The sixth and subsequent bubbles condense upon contact with the oil. |

The minimum level of enrichment required to render the methane miscible in the crude oil is determined to be a 0.12 fraction ethane in methane.

While the foregoing preferred embodiment of the invention has been described and shown, it is understood that the alternatives and modifications, such as those suggested and others, may be made thereto and fall within the scope of the invention.

We claim:

1. A method for determining the minimum level of enrichment required to render a substantially immiscible bulk gas miscible in a liquid hydrocarbon wherein a transparent tube contains a sample of said liquid hydrocarbon, the method comprising the steps of:
   (a) maintaining said liquid hydrocarbon sample at a predetermined substantially constant temperature and pressure;
   (b) forming a plurality of visible enriched gas bubbles comprised of said bulk gas and an enriching fluid, wherein the level of enrichment of said enriched gas is substantially below said minimum level of enrichment;
   (c) sequentially discharging said plurality of gas bubbles into one end of said liquid sample contained in said tube;
   (d) propelling said plurality of gas bubbles from said one end of said sample to the other end of said sample such that each gas bubble continuously and visibly contacts said liquid sample;
   (e) visually observing said plurality of bubbles as it is propelled through said liquid sample;
   (f) maintaining a fresh sample of said liquid hydrocarbon at said predetermined substantially constant temperature and pressure;
   (g) forming a second plurality of visible enriched gas bubbles, having an incrementally higher level of enrichment than said first plurality of enriched gas bubbles, and repeating steps c, d, and e for said second plurality of bubbles in said fresh sample of liquid hydrocarbon;
   (h) repeating steps f and g, each time forming a plurality of enriched gas bubbles having an incrementally higher level of enrichment than said previous plurality of bubbles until at least one bubble of said plurality is observed to substantially dissipate into said liquid hydrocarbon sample at a given level of enrichment; and (i) determining said given level of enrichment at which said at least one bubble substantially dissipates in said liquid hydrocarbon sample to be said minimum level of enrichment required to render said bulk gas miscible in said liquid hydrocarbon.

2. The method of claim 1 wherein said predetermined pressure is maintained on said liquid sample by means of a hydraulic fluid.

3. The process of claim 2 wherein said tube has an upper section and a lower section and wherein said upper section contains said liquid sample and said lower section contains said hydraulic fluid.

4. The process of claim 2 wherein said plurality of bubbles is formed in said hydraulic fluid.

5. The process of claim 4 wherein said plurality of bubbles is formed in said lower section of said tube.

6. The process of claim 1 wherein said liquid sample is a crude oil.

7. The process of claim 2 wherein the interfacial tension between said hydraulic fluid and said gas is greater than the interfacial tension between said liquid sample and said gas.

8. The process of claim 2 wherein said hydraulic fluid is water.

9. The process of claim 2 wherein said predetermined pressure is maintained by pressurized gas head on said hydraulic fluid.

10. The process of claim 1 wherein said plurality of bubbles is propelled through said liquid by a buoyant force on said bubbles.

11. The process of claim 10 wherein the longitudinal axis of said tube is aligned at an angle deviating from the horizontal.

12. The process of claim 11 wherein said angle is selected to determine the time that said gas contacts said liquid.

13. The process of claim 11 wherein the longitudinal axis of said tube is aligned 90° from the horizontal.

14. The process of claim 3 wherein said upper section of said tube has an elongated cross-section and said plurality of gas bubbles substantially and continuously contacts an interior wall of said upper section.

15. The method of claim 1 wherein said bulk gas is substantially less miscible than said enriching fluid in said liquid hydrocarbon.

16. The method of claim 1 wherein said bulk gas is selected from the group consisting of carbon dioxide, nitrogen, sulfur dioxide, methane, and mixtures thereof.

17. The method of claim 1 wherein said enriching fluid is selected from the group consisting of ethane, propane, butane, pentane, and mixtures thereof.

18. The method of claim 1 wherein said enriching fluid is substantially miscible in said bulk gas at said substantially constant temperature and pressure.

19. A method for predetermining the minimum level of enrichment required for an enriched gas to sustain a miscible condensing gas drive for the recovery of a crude oil from a subterranean oil-bearing formation having a temperature and a fracturing pressure, comprising the steps of:
(a) maintaining a sample of said crude oil in a transparent tube at said substantially constant formation temperature and a pressure substantially below said formation fracturing pressure;
(b) forming a plurality of visible enriched gas bubbles comprised of a bulk gas and an enriching fluid, wherein the level of enrichment of said enriched gas is substantially below said minimum level of enrichment;
(c) sequentially discharging said plurality of gas bubbles into one end of said sample contained in said tube;
(d) propelling said plurality of gas bubbles from said one end of said sample to the other end of said sample such that each gas bubble continuously and visibly contacts said crude oil sample;
(e) visually observing said plurality of bubbles as it is propelled through said sample;
(f) maintaining a fresh sample of said crude oil at said substantially constant formation temperature and said pressure substantially below said formation fracturing pressure;
(g) forming a second plurality of visible enriched gas bubbles having an incrementally higher level of enrichment than said first plurality of enriched gas bubbles and repeating steps c, d, and e for said second plurality of gas bubbles in said fresh sample of crude oil;
(h) repeating steps f and g, each time forming a plurality of enriched gas bubbles having an incrementally higher level of enrichment than said previous plurality of bubbles until at least one bubble of said plurality is observed to substantially dissipate in said crude oil sample at a given level of enrichment; and
(i) determining said given level of enrichment at which said at least one bubble substantially dissipates in said crude oil sample to be said minimum level of enrichment required for said enriched gas to sustain said miscible condensing gas drive for the recovery of said crude oil from said subterranean oil-bearing formation.

20. The method of claim 19 wherein said predetermined pressure is maintained on said crude oil sample by means of a hydraulic fluid.

21. The process of claim 20 wherein said tube has an upper section and a lower section and wherein said upper section contains said crude oil sample and said lower section contains said hydraulic fluid.

22. The process of claim 20 wherein said plurality of gas bubbles is formed in said hydraulic fluid.

23. The process of claim 22 wherein said plurality of gas bubbles is formed in said lower section of said tube.

24. The process of claim 20 wherein the interfacial tension between said hydraulic fluid and said gas is greater than the interfacial tension between said crude oil sample and said gas.

25. The process of claim 20 wherein said hydraulic fluid is water.

26. The process of claim 20 wherein said predetermined pressure is maintained by a pressurized gas head on said hydraulic fluid.

27. The process of claim 19 wherein said plurality of bubbles is propelled through said crude oil by a buoyant force on said bubbles.

28. The process of claim 27 wherein the longitudinal axis of said tube is aligned at an angle deviating from the horizontal.

29. The process of claim 28 wherein said angle is selected to determine the time that said gas contacts said crude oil.

30. The process of claim 28 wherein the longitudinal axis of said tube is aligned 90° from the horizontal.

31. The process of claim 21 wherein said upper section of said tube has an elongated cross-section and said plurality of gas bubbles substantially and continuously contacts an interior wall of said upper section.

32. The method of claim 19 wherein said bulk gas is substantially less miscible than said enriching fluid in said crude oil.

33. The method of claim 19 wherein said bulk gas is selected from the group consisting of carbon dioxide, nitrogen, sulfur dioxide, methane, and mixtures thereof.

34. The method of claim 19 wherein said enriching fluid is selected from the group consisting of ethane, propane, butane, pentane, and mixtures thereof.

35. The method of claim 19 wherein said enriching fluid is substantially miscible in said bulk gas at said substantially constant formation temperature and said pressure substantially below said formation fracturing pressure.

* * * * *